United States Patent
Doshi et al.

(10) Patent No.: US 7,157,100 B2
(45) Date of Patent: Jan. 2, 2007

(54) PHARMACEUTICAL COMPOSITION FOR CONTROLLED DRUG DELIVERY SYSTEM

(75) Inventors: Madhukat Mansukhlal Doshi, Maharashtra (IN); Milind Dattatraya Joshi, Maharashtra (IN); Bharat Pravinchandra Mehta, Maharashtra (IN)

(73) Assignee: J.B. Chemicals & Pharmaceuticals Ltd., Mumbai (IN)

( * ) Notice: Subject to any disclaimer, the term of this patent is extended or adjusted under 35 U.S.C. 154(b) by 350 days.

(21) Appl. No.: 10/172,125

(22) Filed: Jun. 14, 2002

(65) Prior Publication Data

US 2003/0232081 A1 Dec. 18, 2003

(51) Int. Cl.
*A61K 9/24* (2006.01)
*A61K 9/46* (2006.01)
*A61K 9/20* (2006.01)

(52) U.S. Cl. ............. 424/472; 424/468; 424/465

(58) Field of Classification Search ............. 424/468, 424/465, 472
See application file for complete search history.

(56) References Cited

U.S. PATENT DOCUMENTS

| 4,140,755 | A | * | 2/1979 | Sheth et al. | 424/472 |
|---|---|---|---|---|---|
| 6,049,177 | A | * | 4/2000 | Felper | 315/219 |
| 6,753,011 | B1 | * | 6/2004 | Faour | 424/473 |
| 2003/0104052 | A1 | * | 6/2003 | Berner et al. | 424/468 |

* cited by examiner

*Primary Examiner*—Vickie Kim
(74) *Attorney, Agent, or Firm*—J. Harold Nissen; Lackenbach Siegel, LLP

(57) ABSTRACT

The present invention describes a novel controlled release multilayer composition that is capable of delivering a first active agent from one layer immediately followed by continuous controlled delivery of second active agent from matrix forming layer while the dosage form floats and is retained in the fluid of the environment. The floating bilayer system comprises of immediate release layer containing one active agent and a disintegrating agent whereas second floating matrix forming layer comprises a gas generating component, a gelling agent, and a second active agent. The present invention relates more particularly to a controlled release fluoroquinolone compositions, which maintain a therapeutically effective blood concentration of fluoroquinolone for duration with once a day administration.

40 Claims, No Drawings

PHARMACEUTICAL COMPOSITION FOR CONTROLLED DRUG DELIVERY SYSTEM

BACKGROUND OF THE INVENTION

1. Field of the Invention

This invention generally relates to novel pharmaceutical compositions for oral administration. This invention relates in particular to such compositions in the form of floating bilayer controlled release system for delivery of one or more active agents.

This invention relates more particularly to immediate delivery of a first active agent followed by continuous controlled delivery of a second agent, which may be same or different from the first active agent, while the system or dosage form floats in the fluid of the environment (e.g., the stomach), thereby being retained in the environment of use for an extended period of time.

2. Description of the Prior Art

Various proposals have been made to achieve controlled release pharmaceutical compositions to slow down the release rate of a drug from preparations so that therapeutically active concentrations are maintained in the body for longer time. In recent years, there have been numerous developments in polymeric carriers and controlled release systems such as films with the drug in a polymer matrix, monolithic devices, reservoir device, microparticles, microspheres or nanoparticles in the form of reservoir and matrix devices, osmotic pumps, pH dependant coatings, soluble polymers with covalently attached 'pendant' drug molecules.

Oral route is the most preferred route of administration for various types of active agents however few active agents exhibit a "small absorption window" in gastrointestinal tract i.e. they are more effectively absorbed only from stomach, duodenum, and initial portion of small intestine. (e.g. methyl dopa, captopril) Hence, in case of such active agents to achieve maximum absorption, it is mandatory to retain these drugs in stomach for extended period of time.

Some active agents are intended for exerting a medical action at gastric level e.g. antibiotics like ofloxacin, ciprofloxacin in the treatment of *H. pylori* infection, antacids, proton pump inhibitors and $H_2$ receptor antagonists. In order to achieve maximum therapeutic efficacy, it is beneficial to maintain such drugs in close proximity to gastric mucosa.

There also exists a requirement of therapeutic cases wherein administration (as acute/symptomatic treatment) of a first therapeutically effective dose of an active agent is required whereas in following steps, slow administration of maintenance dose of the same or different drug is necessary. These types of therapeutic needs result in complicated dosage regimen that are not always correctly adhered to by the patients especially the outpatients. Non compliance with dosage regimen is directly proportional to complexity and no. of daily doses.

The major concern with antibiotic therapy is development of resistance by microorganisms. The variation in the antibiotic drug concentrations in the body fluid after conventional drug therapy leads to development of resistance by microorganisms. Many a times this problem is further aggravated due to patient non-compliance due to missed doses.

Fluoroquinolones are one of the most widely used in the management of infectious diseases. Their potent and broad spectrum of activity, efficacy and relative safety make them useful for both community acquired and nosocomial infections. However, inappropriate prescribing and missed posology can lead to antimicrobial resistance.

The candidates representing fluoroquinolone class are ciprofloxacin, ofloxacin, pefloxacin, grepafloxacin, enoxacin, amifloxacin, fleroxacin, temafloxacin, lomefloxacin, norfloxacin, sparfloxacin, levofloxacin, gatifloxacin and moxifloxacin. Ciprofloxacin and ofloxacin have exhibited wide spectrum of antimicrobial activity.

The present invention will be further elaborated with exemplifications with ciprofloxacin and ofloxacin those being the representative candidates of fluoroquinolone group but the scope of the invention is not limitative thereof.

Ciprofloxacin is 1-cyclopropyl-6-fluoro-1, 4-drhydro-4-oxo-7-(1-piperazinyl)-3-quinoline carboxylic acid. It is a faintly yellowish to light yellow crystalline substance. Ciprofloxacin differs from other quinolones in that it has a fluorine atom at the 6-position, a piperazine moiety at the 7-position, and a cyclopropyl ring at the 1-position. The recommended adult dosage 500-mg every 12 hours. The usual duration of treatment is 7–14 days.

An important factor affecting the absorption of orally administered drug through gastrointestinal tract is transit time in gastrointestinal tract. Ciprofloxacin is absorbed only from the stomach to the jejunum. Hence to achieve maximum efficacy it would be beneficial if the drug is retained in stomach for extended period of time. This problem can be overcome by developing a system that is retained in stomach for prolonged time and can release active agent in a controlled manner.

Another widely used fluororquinolone candidate, ofloxacin is the racemate, (±)-9-fluoro-2,3-dihydro-3-methyl-10-(4-methyl-1-piperazinyl)-7-oxo-7H-pyrido [1,2,3-de]-1,4-benzo-xazine-6-carboxylic acid. Ofloxacin is an off-white to pale yellow crystalline powder. The molecule exists as a zwitterion at the pH conditions in the small intestine. The relative solubility characteristics of ofloxacin at room temperature indicate that ofloxacin is considered to be soluble in aqueous solutions with pH between 2 and 5. It is sparingly to slightly soluble in aqueous solutions with pH 7 and freely soluble in aqueous solutions with pH above 9. The usual dose of ofloxacin is 200 mg to 400 mg every 12 hours and the usual duration of treatment is 7–10 days. Considering the maximum solubility of drug, it would be more beneficial to retain the drug in stomach for prolonged duration so as to achieve maximum absorption.

As described above and exemplified with the two leading fluoroquinolone derivatives, the efficacy and patient compliance of the fluoroquinolones and similar drugs can be improved by retaining the compositions in stomach for longer time. To facilitate their longer duration of treatments and to avoid variation in drug concentrations in the body (which occurs with conventional therapy) it is further desirable to extend the release of drug that would lead to better patient compliance and success of therapy.

Thus, in the view of the above discussion it can be concluded that to achieve maximum efficacy of the fluoroquinolone derivatives it is desirable to retain the active agents in stomach and acquire uniform continuous release of the same in a controlled manner. It is also desirable to avoid the initial lag time in the release of antibiotic from controlled release composition hence the pharmaceutical composition of the present invention is designed to have an initial loading dose as an immediate release form.

The concept of bilayer tablet is well known in the art which is generally employed for various purposes such as stabilization (U.S. Pat. No. 6,287,600), taste masking (U.S. Pat. No. 5,690,959) or delivering two drugs having synergistic effects (U.S. Pat. No. 6,319,519). Bastin described use of bilayer tablet for administration of drugs prone to abuse where the drug layer and gelling layer are separate and the concentration of gelling agent is such that it doesn't retard release of active agent but facilitates drug release similar to that of conventional tablet. Blume (U.S. Pat. No. 6,372,252) discloses guaifenesin sustained release bilayer tablet offering bioavailability of drug for 12 hours where first portion is of immediate release and second is for controlled release. The release is not site specific.

Several literatures describe buoyant dosage forms which improve gastric residence time. Most of the patents disclose monolithic systems (U.S. Pat. Nos. 4,126,672 and 4,167,558). U.S. Pat. Nos. 4,814,178 and 4,814,179 describe non-complexed sustained release floating tablets including hydrocolloid gelling agent, oil, selected therapeutic agent, water and have multitudes of air holes with density less than 1. These systems are not restricted to floating in gastric fluid. U.S. Pat. No. 4,140,755 discloses two layered buoyant tablet containing antacid where one layer is formulated to immediately release the active and other to obtain density lower than gastric fluid and provide controlled release of drug. Franz (U.S. Pat. No. 5,232,704) discloses sustained release bilayer formulation where one layer is drug release layer and other is a floating layer which releases all the drug over a extended period in stomach. Conte et al (U.S. Pat. No. 5,681,583) disclosed pharmaceutical multilayered tablet which exhibited high volume increase in contact with biological fluid, increasing volume of tablet and retaining the dosage form in stomach. Dennis (U.S. Pat. No. 5,169,638) described buoyant controlled release powder formulation comprising basic active agent, salt of alginic acid and hydrocarbon gelling agent. Alza corporation (U.S. Pat. Nos. 4,036,228, 4,847,093, 4,344,929) describe osmotic device containing gas generating agent and releasing drug as a effervescent generated fine dispersion over osmotic gradient. U.S. Pat. No. 4,777,033 discloses oral compositions containing sodium bicarbonate as gas generating agent along with hydrocolloid polymer which offers buoyancy to the system and releasing drug in a controlled manner but not specific to stomach.

All the above systems describe either bilayer tablets or gastro-retentive compositions or combined bilayer gastro-retentive formulation which are either intended for immediate release, or only for controlled delivery of drugs which pose problems of bioavailibility fluctuations. To overcome these insufficiencies, the inventors of the present invention have come out with a novel pharmaceutical composition of floating bilayer system wherein the first layer is designed to release active agent immediately avoiding lag time in the therapy and the matrix forming second layer that releases drug in a controlled manner while the system floats in gastric environment.

The present invention relates to a controlled release fluoroquinolone formulation for oral administration and methods of its manufacture. In particular, it relates to a controlled release fluoroquinolone formulation which maintains a therapeutically effective blood concentration of fluoroquinolone with once a day administration. The present invention further relates to a modified release bi-layer fluoroquinolone tablet which demonstrates a maximum serum concentration equivalent to an immediate release tablet yet maintains a therapeutically effective blood concentration with once a day administration.

SUMMARY OF THE INVENTION

It is an object of this invention to provide a novel solid pharmaceutical composition for oral administration in the form of floating bilayer system that allows immediate delivery of one active agent followed by release of second active agent from specialized matrix forming layer which causes the system to float.

It is another object of the present invention to provide a drug delivery system that exhibits immediate release of one active ingredient present in one layer followed by controlled release of second active agent incorporated in second layer which can be same or different than the first one.

It is also an object of the invention to provide a drug delivery system for delivering fluoroquinolone derivatives that floats and thereby is retained in the stomach It is a further object of the present invention to provide such a composition, which releases active agent from one layer instantaneously due to rapid disintegration of the layer in the fluid of the environment of use.

It is yet another object of the present invention to develop a bilayer system where a gas generating component of a second layer produces gas which gets entrapped by swollen gelled hydrophilic matrix thus causing the system to float, retain in the stomach and release the active agent in a controlled manner from the matrix.

It is yet another object of the present invention to develop a floating bilayer system for delivering fluoroquinolone derivatives that maintains therapeutically active concentrations of fluoroquinolones with once a day administration thus leading to better patient compliance.

Thus, the pharmaceutical bilayer composition as described in the present invention is effective for immediate release of active agent from one layer followed by continuous, controlled delivery of active agent present in second layer which is capable of acting locally in gastrointestinal tract or acting systemically by absorption via stomach and upper part of the intestine which can be same or different than the first active. The rate at which the drug from the second matrix forming controlled release layer is released depends on the rate of diffusion of the active agent through swollen polymeric matrix.

Other features, advantages and objectives of this invention and its preferred embodiments will become apparent from the detailed description and accompanying claims, which follow.

DETAILED DESCRIPTION OF THE INVENTION

The present invention is a novel solid pharmaceutical composition in the form of a floating bilayer system for oral administration that is adapted to deliver a first active agent from an first layer immediately upon reaching the gastrointestinal tract, and deliver a second active agent from a second layer which may be same or different, in a controlled manner over a specific time period. The second layer is also adapted to provide buoyancy for the device, thereby making the device effectively float and remain in the stomach.

The present invention provides a solid pharmaceutical composition for oral administration containing two or more layers comprising of a) At least one layer containing an active agent and disintegrating agent intended for immediate delivery, b) at least one second layer that includes an active agent for controlled drug delivery, gas generating component, a matrix forming gelling agent which is intended for controlled delivery of active agent to maintain therapeutic effective concentrations with once a day administration in human body and also be administered to veterinary class with appropriate modifications.

c) An optional third layer placed between the above two layers comprising an inert excipients selected from lactose, mannitol, microcrystalline cellulose, starch, dicalcium phosphate, the layer physically separates the other two layers and facilitates delivery of two incompatible active agents.

The said composition of the present invention on oral ingestion, comes in contact with gastric fluid, the first layer disintegrates rapidly releasing the active ingredient instantaneously, the second layer considerably swells and gels in presence of fluid of the environment resulting in volume expansion entrapping the gas generated by the reaction of gas generating component and fluid of the environment, thus, releasing the active agent from second layer which may be same or different, in a controlled manner while the system floats in gastric environment.

The preferred embodiment of the present invention wherein solid pharmaceutical composition is preferably a bilayer tablet and two layers are distinguished by different colors.

A preferred embodiment of the present invention comprises about 5% to about 80% of an total active ingredient, more preferably about 25% to 75% and the most preferably about 72% of the total active agent by weight based on the total weight of the composition.

The active agent preferably present in the first layer is in the range of about 2% to 20%, more preferably between 5% to 17% and most preferably about 10% of the active agent by weight based on the total weight of the composition.

The preferred ratio of active agent in immediate layer to that in controlled release layer is in the range of 1:1 to about 1:12 and more preferably from about 1:3 to about 1:10.

A first layer of the preferred embodiment of the present invention comprises of a disintegrating agent which can be selected from group of starch, sodium starch glycolate, pregelatinised starch, crosslinked poly vinyl pyrrolidone, cross linked carboxy methyl cellulose, ion exchange resin, the most preferred being sodium starch glycolate. Sodium starch glycolate helps in rapid disintegration of the first layer as the system comes in contact with the fluid of the environment thus releasing the active agent instantaneously. Sodium starch glycolate is present in an amount ranging from about 0.25% to 2.5%, more preferably 0.5 to 2.0% and most preferably is about 1% by weight based on the total weight of the composition.

The second layer of the preferred embodiment of the present invention comprises about 45% to about 75% of an active ingredient, more preferably about 50% to 70% and most preferably is about 62% by weight based on the total weight of the composition along with about 2% to about 15% of a gas generating material, about 5% to about 20% of a gelling agent. As used herein, percentage amounts for an ingredient are the percent weights of the ingredients based on the total weight of the composition, which may be abbreviated as "% w/w."

The active agent as described in the present invention comprises therapeutic compounds which can be formulated into the present floating bilayer system include ACE inhibitor, alcohol abuse preparation, alpha adrenergic agonist, amoebicide, analgesics, anti-inflammatory agents, anthelmintics, anti-arrhythmic agents, anti-bacterial agents, anti-viral agents, anti-coagulants, anti-depressants, anti-diabetics, anti-diuretics, anti-emetic, anti-epileptics, anti-flatulent, anti-viral, anti-fungal agents, anti-gout agents, anti-hypertensive agents, anti-malarials, anti-migraine agents, anti-muscarinic agents, anti-neoplastic agents, anti-parkinson agents, anti-psychotic, anti-pyretic, obesity management agents, anti-asthematics, immunosuppressants, anti-protozoal agents, anti-thyroid agents, anti-tussives, anxiolytic, sedatives, hypnotics, neuroleptics, beta-Blockers, cardiac inotropic agents, corticosteriods, diuretics, gastro-intestinal agents, histamine receptor antagonists, norcotics, NSAIDs, anorectics, anorexiants, antacid, blood modifiers, anti convulsant, bone metabolism regulators, bronchial dialators, calcium channel blockers, beta adregeneic blockers, diuretics, CNS agents, cough preparations, erectile dysfunction therapeutic agent, lipid regulating agents, muscle relaxants, anti-anginal agents, psychotherapeutic agents, osteoporosis preparations, respiratory agents, nutritional agents, anti convulsant, smoking cessation agents, thyroid preparation, sex hormones, stimulants, urinary tract agents, uterine contractors, and mixtures thereof. The pharmaceutical composition as described in the present invention can be employed for any new active ingredients for human as well as veterinary use which would be invented in future, with appropriate modifications and not limited only to the catagories mentioned above.

The preferred embodiment of the present invention comprising the active agent for controlled delivery and the active agent for immediate delivery may exhibit small absorption window in gastrointestinal tract.

The active ingredient present in the first immediate layer and the active ingredient present in the second controlled release layer of the floating bilayer system of the present invention may be same or different. In case of the preferred embodiments of the present invention both the drugs are the same.

The preferred embodiment of the present invention comprising the active agent is preferably selected from group of fluoroquinolone antibiotic such as ciprofloxacin, ofloxacin, pefloxacin, grepafloxacin, enoxacin, amifloxacin, fleroxacin, temafloxacin, lomefloxacin, levofloxacin, norfloxacin, sparfloxacin, trovafloxacin, gatifloxacin and moxifloxacin.

The second layer of the pharmaceutical composition of the present invention comprises gas generating component which generates gas on contact with gastric fluid and is selected from group of water soluble carbonates, sulfites and bicarbonates such as sodium carbonate, sodium bicarbonate, sodium metabisulfite, calcium carbonate. The most preferred being sodium bicarbonate and is present in an amount from about 2% to 15%, preferably from about 5.0% to 10.0% and the most preferred is about 7% by weight based on the total weight of the composition. The gas generating component upon interaction with gastric fluid generates carbon dioxide or sulfur dioxide that gets entrapped within hydrated gel matrix of the gelling agent. The amount of gas generating component present is at least 7.5% of the concentration of the active agent present in the second layer and more preferably about 10%.

The second controlled release layer of the pharmaceutical composition of the present invention contains one or more matrix forming gelling agents selected from group consisting of hydroxypropyl methylcellulose, methylcellulose, hydroxypropyl cellulose, carbomer, carboxy methylcellulose, gum tragacanth, gum acacia, guar gum, pectin, modified starch derivatives, xanthan gum, locusta bean gum, sodium alginate, the most preferred being hydroxypropyl methylcellulose i.e. Methocel® which on contact with gastric fluid swells and gels, forming matrix structure that entraps the gas released and also release the active agent in a controlled manner.

The most preferred matrix forming gelling agent of the present invention is hydroxypropyl methylcellulose which has a viscosity in the range from 4,000 cps to about 100,000 cps. The concentration of the matrix forming gelling agent is from about 5% to about 20.0% and a more preferred range being 7.5% to 15%, and the most preferred range being 10% by weight based on the total weight of the composition. The preferred embodiment of the present invention contains a combination of matrix forming gelling agents comprising of methyl cellulose (viscosity 3000–5600 cP) available under the trademark Methocel® K4M and methyl cellulose (viscosity 80000–120000 cP) available under the trademark Methocel® K100M. The ratio between the concentration of Methocel® K4M to Methocel® K 100M is in the range of 1:0.25 to about 1:5.

The pharmaceutical composition of the present invention can also comprise any other suitable ingredient well known to those skilled in the art, such as adsorbents, fillers, antioxidants, buffering agents, colorants, flavorants, sweetening agents, tablet antiadherents, lubricants, tablet binders, diluents, tablet direct compression excipients, tablet disintegrants, tablet glidants, polishing agents, and other equivalent excipients selected from the group consisting of magnesium stearate, calcium stearate, zinc stearate, powdered stearic acid, hydrogenated vegetable oils, talc, polyethylene glycol, mineral oil, an FD&C color, modified cellulose, lactose, gelatin, starch paste, acacia, tragacanth, povidone, polyethylene glycol, colloidal silicon dioxide, talc, sodium lauryl sulfate, quaternary ammonium salts, mannitol, sodium chloride, sodium sulfate, sodium phosphate, magnesium chloride, magnesium sulfate, magnesium phosphate, microcrystalline cellulose, sodium starch glycolate, lactose, microcrystalline cellulose, sucrose, glucose, mannitol, calcium carbonate, colloidal anhydrous silica, polyethylene glycols, waxes, hydrogenated castor oil, starch, polyvinyl pyrrolidone and a combination thereof.

Furthermore, preferred embodiments of the present invention may be coated with a polymeric film merely to provide protection from moisture. The said coating polymer is selected from a group of hydroxypropyl methylcellulose, hydroxypropyl cellulose, polyvinyl pyrrolidone, polyvinyl alcohol or methacrylic acid polymer, and the most preferred being methacrylic acid copolymer available under the trademark Eudragit E 100®. The said coating is transparent, soluble in fluid of the environment i.e. soluble in acidic pH and does not retard the release of active agent. The coating imparts moisture barrier properties to increase stability.

The solid pharmaceutical composition of the present invention is coated and the most preferred polymer for coating is a methacrylic acid copolymer available under the trademark Eudragit® E 100 which copolymer is present in a concentration of from about 1% to about 5.0%, and the most preferred concentration is about 2% by weight based on the total weight of the composition.

The pharmaceutical composition as described by the present invention is prepared by process as described below:

Preparation of Immediate Release Granule I:

The granules can be prepared either by process A or B as described below.

Process A:
a) The active agent, microcrystallline cellulose, colloidal anhydrous silica, colour are sifted through 40# sieve and mixed in a suitable mixer for 10 minutes.
b) The blend is granulated with warm water (50–55°) by mechanical means.
c) Granules are dried at 45–50° C. till LOD is between 2–3% w/w.
d) Dried granules are mechanically sifted through 30# sieve.
e) The granules are lubricated with mixture of sodium starch glycolate, colloidal anhydrous silica, colour, magnesium stearate (presifted through 40#) by mechanical mixing.

Process B:
a) The active agent, microcrystalline cellulose, colloidal anhydrous silica, colour, sodium starch glycolate, colloidal anhydrous silica, colour, magnesium stearate are sifted through 40# sieve and mixed in a suitable mixer for 10 minutes.
b) The blend is slugged on rotary compression machine or compacted using roll compactor
c) The slugs or compacts are sifted through 30# sieve to obtain fine granules.
c) The granules are further lubricated with part of the magnesium stearate (presifted through 40#) by mechanical mixing.

Preparation of Floating Controlled Release Granules II:

The granules can be prepared either by process A or B as described below:

process A to form Granule I:
a) an active agent, methyl cellulose (viscosity 3000–5600 cP) available under the trademark Methocel® K 4M, and another active agent methyl cellulose (viscosity 80000–120000 cP) available under the trademark Methocel® K100M, and lactose are sifted through a 30# sieve and mixed by mechanical means in an area with a controlled temperature and humidity;
b) the blend is granulated using water and granules which are dried at 40–50° C.; and
c) the dried granules are sifted through a 30# sieve and lubricated with sodium bicarbonate, talc and magnesium stearate (which are presifted through 40# sieve);

process B to form Granule II:
a) active agents methyl cellulose (viscosity 3000–5600 cP) available under the trademark Methocel® K 4M, and methyl cellulose (viscosity 80000–120000 cP) available under the trademark Methocel® K 100M, and lactose, sodium bicarbonate, talc and magnesium stearate are sifted through a 30# sieve and mixed by mechanical means in an area with a controlled temperature and humidity; and
b) the blend is dry granulated and sifted through 20# sieve;

compression:
Granules I & II are compressed on a bilayer tablet compression machine;

coating:
an appropriate quantity of methacrylic acid copolymer available under the trademark Eudragit® E 100 is dissolved in blend of Isopropyl alcohol, dichloromethane water under stirring to get clear solution, and then the solution is strained through 100# and used for film coating of bilayer tablets.

The most preferred process being process A for preparation of immediate release and controlled release granules.

The invention will be more fully understood from the following examples. These examples are to be constructed as illustrative of the invention and not limitative thereof:

EXAMPLE 1

Ofloxacin

Example 1 discloses a floating bilayer system according to the present invention wherein the active agent is Ofloxacin, which is required for the treatment of local action on *H. pylori* in the stomach.

|    |                                                                                              | % w/w |
| -- | -------------------------------------------------------------------------------------------- | ----- |
| 1. | Ingredients of Immediate layer                                                               |       |
|    | Ofloxacin                                                                                    | 7.0   |
|    | Microcrystalline cellulose                                                                   | 1.5   |
|    | Anhydrous Colloidal Silica                                                                   | 1.0   |
|    | Color iron oxide yellow                                                                      | 1.0   |
|    | Sodium starch glycolate                                                                      | 1.0   |
|    | Magnesium stearate                                                                           | 0.5   |
| 2. | Ingredients of Controlled release layer                                                      |       |
|    | Ofloxacin                                                                                    | 63.0  |
|    | Methyl Cellulose (Viscosity 80000–120000 cp) available under the trademark Methocel® K 100 M | 6.0   |
|    | Methyl Cellulose (Viscosity 3000–5600 cp) available under the trademark Methocel® K 4 M      | 4.0   |
|    | Sodium bicarbonate                                                                           | 7.0   |
|    | Lactose                                                                                      | 4.0   |
|    | Talc                                                                                         | 1.0   |
|    | Magnesium stearate                                                                           | 1.0   |
| 3. | Coating                                                                                      |       |
|    | Methacrylic and copolymer available under trademark Eudragit® E 100                          | 2.0   |

The tablet of Example 1 is prepared by following process

Preparation of Immediate Release Granule I:

a) Ofloxacin, microcrystalline cellulose, colloidal anhydrous silica, colour are sifted through 40# sieve and mixed in a suitable mixer for 10 minutes.
b) The blend is granulated with warm water (50–55°) by mechanical means.
c) Granules are dried at 45–50° C. till LOD is between 2–3% w/w.
d) Dried granules are mechanically sifted through 30# sieve.
e) The granules are lubricated with mixture of sodium starch glycolate, colloidal anhydrous silica, colour, magnesium stearate (presifted through 40#) by mechanical mixing.

Preparation of Floating Controlled Release Granules II:

a) ofloxacin, methyl cellulose (viscosity 3000–5600 cP) available under the trademark Methocel® K 4M, methyl cellulose (viscosity 80000–120000 cP) available under the trademark Methocel® K100M, lactose are sifted through 30# sieve and mixed by mechanical means in an area with a controlled temperature and humidity;
b) the blend is granulated using water and granules are dried at 45–50° C.; and
c) the dried granules are sifted through 30# sieve and lubricated with sodium bicarbonate, talc and magnesium stearate (presifted through 40# sieve).

Compression:

Granules I & II are compressed on Manesty bilayer tablet compression machine.

Coating:

an appropriate quantity of methacrylic acid copolymer available under the trademark Eudragit® E 100 is dissolved in a blend of Isopropyl alcohol, dichloromethane water under stirring to get clear solution. The solution is strained through a 100# sieve and used for film coating of bilayer tablets.

The tablet of Example 1 was tested for dissolution in 0.1N HCl using USP apparatus 1 at 100 rpm. The release profile is as follows:

| Time (hrs.) | Ofloxacin released (cumulative %) |
| ----------- | --------------------------------- |
| 1           | 24.25                             |
| 2           | 33.22                             |
| 4           | 50.0                              |
| 8           | 67.72                             |
| 16          | 94.30                             |

EXAMPLE 2

Example 2 discloses a floating bilayer system according to the present invention wherein the active agent is ciprofloxacin, which is required for systemic action and absorbed only from the upper part of gastrointestinal tract.

|    |                                                                                              | % w/w |
| -- | -------------------------------------------------------------------------------------------- | ----- |
| 1. | Ingredients of Immediate layer                                                               |       |
|    | Ciprofloxacin base                                                                           | 15.0  |
|    | Microcrystalline cellulose                                                                   | 2.0   |
|    | Anhydrous Colloidal Silica                                                                   | 0.95  |
|    | Color iron oxide yellow                                                                      | 1.0   |
|    | Crosslinked polyvinyl pyrrolidone                                                            | 0.89  |
|    | Starch 1500                                                                                  | 1.0   |
|    | Magnesium stearate                                                                           | 0.4   |
| 2. | Ingredients of Controlled release layer                                                      |       |
|    | Ciprofloxacin base                                                                           | 60.0  |
|    | Methyl Cellulose (Viscosity 3000–5600 cp) available under the trademark Methocel® K 4 M      | 3.5   |
|    | Methyl Cellulose (Viscosity 80000–120000 cp) available under the trademark Methocel® K 100 M | 3.5   |
| 3. | Coating                                                                                      |       |
|    | Methacrylic Acid Copolymer available under the trademark Eudragit® E 100                     | 2.0   |

The tablet of Example 2 is prepared by following process

Preparation of Immediate Release Granule I:

a) Ciprofloxacin, microcrystalline cellulose, colloidal anhydrous silica, colour are sifted through 40# sieve and mixed in a suitable mixer for 10 minutes.
b) The blend is granulated using aqueous solution of starch 1500 (50–55°) by mechanical means.
c) Granules are dried at 45–50° C. till LOD is between 2–3% w/w.
d) Dried granules are mechanically sifted through 30# sieve.
e) The granules are lubricated with mixture of croslinked polyvinyl pyrrolidone, colloidal anhydrous silica, colour, magnesium stearate (presifted through 40#) by mechanical mixing.

Preparation of Floating Controlled Release Granules II:

a) ciprofloxacin, methyl cellulose (viscosity 3000–5600 cP) available under the trademark Methocel® K 4M, methyl cellulose (viscosity 80000–120000 cP) available under the trademark Methocel® K100M, lactose are sifted through a 30# sieve and mixed by mechanical means in an area with a controlled temperature and humidity.

b) The blend is granulated using water and granules are dried at 45–50° C.

c) The dried granules are sifted through 30# sieve and lubricated with sodium bicarbonate, talc and magnesium stearate (presifted through 40# sieve).

Compression:

Granules I & II are compressed on Manesty bilayer tablet compression machine.

Coating:

an appropriate quantity of methacrylic acid copolymer available under the trademark Eudragit® E 100 is dissolved in a blend of Isopropyl alcohol, dichloromethane water under stirring to get clear solution. The solution is strained through 10# & used for film coating of bilayer tablets.

The tablet of Example 2 was tested for dissolution in 0.1N HCl using USP apparatus 1 at 100 rpm. The release profile is as follows:

| Time (hrs.) | ciprofloxacin, released (cumulative %) |
|---|---|
| 1 | 21.39 |
| 2 | 39.30 |
| 4 | 52.02 |
| 8 | 72.80 |
| 16 | 89.50 |

EXAMPLE 3

Example 3 discloses a floating bilayer system according to the present invention wherein the active agent is levofloxacin.

| | | % w/w |
|---|---|---|
| 1. | Ingredients of Immediate layer | |
| | Levofloxacin | 6.5 |
| | Microcrystalline cellulose | 2.5 |
| | Anhydrous Colloidal Silica | 1.0 |
| | Color iron oxide yellow | 1.0 |
| | Sodium starch glycolate | 1.2 |
| | Magnesium sterate | 0.4 |
| 2. | Ingredients of Controlled release layer | |
| | Levofloxacin | 62.5 |
| | Methyl Cellulose (Viscosity 80000–120000 cp) available under the trademark Methocel ® K 100 M | 5.0 |
| | Methyl Cellulose (Viscosity 3000–5600 cp) available under the trademark Methocel ® K 4 M | 3.3 |
| | Sodium bicarbonate | 7.5 |
| | Lactose | 5.0 |
| | Talc | 1.1 |
| | Magnesium stearate | 1.0 |
| 3. | Coating | |
| | Methacrylic Acid Copolymer available under the trademark Eudragit ® E 100 | 2.0 |

The tablet of Example 3 is prepared by following process

Preparation of Immediate Release Granule I:

a) Levofloxacin, microcrystalline cellulose, colloidal anhydrous silica, colour are sifted through 40# sieve and mixed in a suitable mixer for 10 minutes.

b) The blend is granulated with warm water (50–55°) by mechanical means.

c) Granules are dried at 45–50° C. till LOD is between 2–3% w/w.

d) Dried granules are mechanically sifted through 30# sieve.

e) The granules are lubricated with mixture of sodium starch glycolate, colloidal anhydrous silica, colour, magnesium stearate (presifted through 40#) by mechanical mixing.

Preparation of Floating Controlled Release Granules II:

a) Levofloxacin, methyl cellulose (viscosity 3000–5600 cP) available under the trademark Methocel® K 4M, methyl cellulose (viscosity 80000–120000 cP) available under the trademark Methocel® K100M, lactose, sodium bicarbonate, talc and stearic acid sifted through a 30# sieve and mixed by mechanical means in an area with a controlled temperature and humidity.

b) The blend is dry granulated and sifted through 20# sieve.

Compression:

Granules I & II are compressed on Manesty bilayer tablet compression machine.

Coating:

an appropriate quantity of methacrylic acid copolymer available under the trademark Eudragit® E 100 is dissolved in a blend of Isopropyl alcohol, dichloromethane water under stirring to get clear solution. The solution is strained through 100# and used for film coating of bilayer tablets.

The tablet of Example 3 was tested for dissolution in 0.1N HCl using USP apparatus 1 at 100 rpm. The release profile is as follows:

| Time (hrs.) | levofloxacin released (cumulative %) |
|---|---|
| 1 | 25.65 |
| 2 | 37.84 |
| 4 | 47.75 |
| 8 | 68.22 |
| 16 | 95.87 |

Thus, compositions according to the present invention do not only provide gastric-retentive dosage forms which release active agents in a controlled manner through an floating bilayer system but also provides initial instantaneous release of active agent avoiding delay in antimicrobial action.

Compositions according to the present invention have an advantage that they may release part of the active agent immediately avoiding lag time and then the compositions may be retained for a long period of time in the stomach of a mammal, thereby delivering an active agent over a period of time that is significant for the clinical need with once a day administration which offers better patient compliance. Also compositions according to the present invention have the advantage that they may provide gastric retention in order to improve the absorption of the active agents which are absorbed only from the stomach to jejunum, and also to offer local treatment in the stomach.

It is to be understood that the examples and embodiments described hereinabove are for the purposes of providing a description of the present invention by way of examples and are not to be viewed as limiting the present invention in any way. It is further to be understood that various changes and modifications may be made to that described in above examples by those of ordinary skill in the art is also contemplated by the present invention and is to be included within the scope of the invention without departing from the scope of the invention.

What is claimed is:

1. A solid pharmaceutical composition for oral administration containing two or more layers forming a modified release bilayer fluoroquinolone tablet maintaining a therapeutically effective concentration with a once a day administration in the form of a floating bilayer controlled release system for the delivery of one or more active agents, comprising:
   a) at least one first controlled release layer containing an active agent and a disintegrating agent intended for immediate delivery and release thereby avoiding lag time; and followed by
   b) at least one second controlled release layer that includes an active agent for continuous controlled drug delivery, gas generating component, a matrix forming gelling agent which is intended for controlled delivery and release of the active agent for controlled drug delivery to maintain therapeutic effective concentrations with the once a day administration in a human body and also can be extended to veterinary use with appropriate modifications; and
   c) a third layer placed between the first and second layers comprising an inert excipients selected from the group consisting of lactose, mannitol, microcrystalline cellulose, starch, and dicalcium phosphate, and the optional third layer physically separates the first and second layers and facilitates delivery of two incompatible active agents wherein one of said active agent is a fluoroquinolone antibiotic.

2. The solid pharmaceutical composition for oral administration according to claim 1, wherein the said composition on oral ingestion, comes into contact with gastric fluid, the first layer disintegrates rapidly releasing the active ingredient instantaneously, the second layer considerably swells and gels in presence of fluid of the environment resulting in volume expansion entrapping the gas generated by the reaction of gas generating component and fluid of the environment, thus, releasing the active agent from said second layer which may be same or different, in a controlled manner while the system floats in a gastric environment.

3. The solid pharmaceutical composition for oral administration according to claim 1, wherein the layers are differentiated by using different colors.

4. The solid pharmaceutical composition for oral administration according to claim 1, wherein the first controlled release layer comprises a disintegrating agent which can be selected from the group consisting of starch, sodium starch glycolate, pregelatinished starch, crosslinked poly vinyl pyrrolidone, cross linked carboxy methyl cellulose, and ion exchange resin.

5. The composition for oral administration according to claim 1, wherein the gas generating component is selected from the group consisting of water soluble carbonates, sulphites, bicarbonates, sodium carbonate, sodium bicarbonate, sodium metabisulphite, calcium carbonate, and combinations thereof, which on contact with gastric fluid releases carbon dioxide or sulphur dioxide gas.

6. The solid pharmaceutical composition for oral administration according to claim 1, wherein the gas generating component is sodium bicarbonate present in an amount from about 2.0% to about 15.0% by weight based on the total weight of the composition.

7. The solid pharmaceutical composition for oral administration according to claim 1, wherein the second controlled release layer contains one or more matrix forming gelling agents selected from group consisting of hydroxypropyl methylcellulose, methylcellulose, hydroxypropyl cellulose, carbomer, carboxy methylcellulose, gum tragacanth, gum acacia, guar gum, pectin, modified starch derivatives, xanthan gum, locusta bean gum, sodium alginate, which on contact with gastric fluid swells and gels, forming matrix structure that entraps the gas released and also releases the active agent in a controlled manner.

8. The solid pharmaceutical composition for oral administration according to claim 1, wherein the matrix forming gelling agent is hydroxypropyl methylcellulose which has a viscosity in the range from 4,000 cps to about 100,000 cps, and concentration of matrix forming polymer is from about 5% to about 20.0% by weight based on the total weight of the composition.

9. The solid pharmaceutical composition for oral administration according to claim 1, wherein the matrix forming gelling agent contains a combination of Methyl Cellulose (Viscosity 3000–5600 cP) and Methyl Cellulose (Viscosity 80000–120000 cP).

10. The solid pharmaceutical composition for oral administration according to claim 1, wherein the gas generating component is adapted to generate a gas in contact with gastric fluid, wherein the gelling agent is adapted to form a substantially gas-impermeable gel matrix in the presence of a fluid, and thereby trapping the gas generated effectively causing the device to float in the fluid while the second active agent is released slowly in a controlled manner.

11. The solid pharmaceutical composition for oral administration according to claim 1, wherein each layer of the said dosage formed additionally comprises an additive selected from the group consisting of magnesium stearate, calcium stearate, zinc stearate, powdered stearic acid, hydrogenated vegetable oils, talc, polyethylene glycol, mineral oil, an FD&C color, modified cellulose, lactose, gelatin, starch paste, acacia, tragacanth, povidone, polyethylene glycol, colloidal silicon dioxide, talc, sodium lauryl sulfate, quaternary ammonium salts, mannitol, sodium chloride, sodium sulfate, sodium phosphate, magnesium chloride, magnesium sulfate, magnesium phosphate, microcrystalline cellulose, sodium starch glycolate, lactose, microcrystalline cellulose, sucrose, glucose, mannitol, calcium carbonate, colloidal anhydrous silica, polyethylene glycols, waxes, hydrogenated castor oil, starch, PVP and a combination thereof.

12. The solid pharmaceutical composition for oral administration according to claim 1, wherein the active agent in the immediate delivery layer and the active agent in the controlled drug delivery layer may be the same or different, and comprises the same active agent in both the layers.

13. The solid pharmaceutical composition for oral administration according to claim 1, wherein the total amount of the active agent is in the range from about 5% to about 80% of a total active ingredient by weight based on the total weight of the composition.

14. The solid pharmaceutical composition for oral administration according to claim 1, wherein said fluoroquinolone antibiotic is selected from the group consisting of ciprofloxacin, ofloxacin, pefloxacin, grepafloxacin, enoxacin, amifloxacin, flerofloxacin, temafloxacin, lomefloxacin, norfloxacin, sparfloxacin, levofloxacin, gatifloxacin and moxifloxacin.

15. The solid pharmaceutical composition for oral administration according to claim 1, wherein the active agent is ofloxacin.

16. The solid pharmaceutical composition for oral administration according to claim 1, wherein the active agent is ciprofloxacin.

17. The solid pharmaceutical composition for oral administration according to claim 1, wherein the system may be coated with a transparent polymeric film merely to provide protection from moisture which does not retard the release; and said coating polymer is selected from the group consisting of hydroxypropyl methylcellulose, hydroxypropyl cellulose, polyvinyl pyrrolidone, polyvinyl alcohol and methacrylic acid polymer.

18. The solid pharmaceutical composition for oral administration according to claim 1, wherein the preferred polymer for coating is methacrylic acid copolymer and is present in concentration from about 1% to about 5.0%.

19. The process of manufacturing the solid pharmaceutical composition for oral administration according to claim 1, is as described below:
   I. preparation of Immediate release granule I:
      a) the active agent, microcrystalline cellulose, colloidal anhydrous silica, colour are sifted through a 40# sieve and mixed in a suitable mixer for 10 minutes;
      b) the blend is granulated with warm water (50–55°) by mechanical means;
      c) granules are dried at 45–50° C. till LOD is between 2–3% w/w;
      d) dried granules are mechanically sifted through a 30# sieve; and
      e) the granules are lubricated with mixture of sodium starch glycolate, colloidal anhydrous silica, colour, magnesium stearate presifted through a 40# by mechanical mixing;
   II. preparation of Floating controlled release Granules II:
      a) active agents, of matrix forming gelling agents, lactose are sifted through a 30# sieve and mixed by mechanical means in an area with a controlled temperature and humidity;
      b) the blend is granulated using water and granules are dried at 45–50° C.; and
      c) the dried granules are sifted through 30# sieve and lubricated with sodium bicarbonate, talc and magnesium stearate (presifted through 40# sieve).
   III. compression:
      granules I and II are compressed on bilayer tablet compression machine.
   IV. coating:
      an appropriate quantity of a polymer selected from the group consisting of hydroxypropyl, methylcellulose, hydroxypropyl cellulose, polyvinyl pyrrolidone, polyvinyl alcohol and methacrylic and polymer is dissolved in a blend of Isopropyl alcohol, dichloromethane water under stirring to get clear solution; and
      the solution is strained through a 100# used for film coating of bilayer tablets.

20. The process of manufacturing the solid pharmaceutical composition for oral administration according to claim 19, wherein the solid pharmaceutical composition for oral administration comprises two or more layers containing:
   a) at least one first layer containing an active agent and a disintegrating agent intended for immediate delivery,
   b) at least one second layer that includes an active agent for controlled drug delivery, gas generating component, a matrix forming gelling agent which is intended for controlled delivery of the last-mentioned active agent to maintain therapeutic effective concentrations with once a day administration in a human body and also can be extended to veterinary use with appropriate modifications;
   c) an optional third layer placed between the above two layers comprising an inert excipients selected from the group consisting of lactose, mannitol, microcrystalline cellulose, starch, dicalcium phosphate, the optional third layer physically separates the other two layers and facilitates delivery of two incompatible active agents.

21. The process of manufacturing the solid pharmaceutical composition for oral administration according to claim 19, wherein the said composition on oral ingestion, comes into contact with gastric fluid, the first layer disintegrates rapidly releasing the active ingredient instantaneously, the second layer considerably swells and gels in presence of fluid of the environment resulting in volume expansion entrapping the gas generated by the reaction of the gas generating component and fluid of the environment, thus, releasing the active agent from second layer which may be the same or different, in a controlled manner while the system floats in gastric environment.

22. The process of manufacturing the solid pharmaceutical composition for oral administration according to claim 19, wherein the solid pharmaceutical composition for oral administration is preferably a bilayer tablet and the layers are differentiated by using different colors.

23. The process of manufacturing the solid pharmaceutical composition for oral administration according to claim 19, wherein the first layer comprises a disintegrating agent which can be selected from the group consisting of starch, sodium starch glycolate, pregelatinished starch, crosslinked polyvinyl pyrrolidone, cross linked carboxy methylcellulose, ion exchange resin, and the sodium starch glycolate is present in an amount ranging from about 0.25% to 2.5 by weight of the total weight of the composition.

24. The process of manufacturing the solid pharmaceutical composition for oral administration according to claim 19, wherein the second controlled release layer contains a gas generating component which can be selected from the group consisting of water soluble carbonates, sulphites, and bicarbonates, sodium carbonate, sodium bicarbonate, sodium metabisulphite, calcium carbonate, and combinations thereof, which on contact with gastric fluid release carbon dioxide or sulphur dioxide gas.

25. The process of manufacturing the solid pharmaceutical composition for oral administration according to claim 19, wherein the gas generating component is sodium bicarbonate present in an amount from about 2.0% to about 15.0 by weight based on the total weight of the composition.

26. The process of manufacturing the solid pharmaceutical composition for oral administration according to claim 19, wherein the second controlled release layer contains one or more matrix forming gelling agents selected from group consisting of hydroxypropyl methylcellulose, methylcellulose, hydroxypropyl cellulose, carbomer, carboxy methylcellulose, gum tragacanth, gum acacia, guar gum, pectin, modified starch derivatives, xanthan gum, locusta bean gum, sodium alginate which on contact with gastric fluid swells and gels, forming matrix structure that entraps the gas released and also releases the active agent in a controlled manner.

27. The process of manufacturing the solid pharmaceutical composition for oral administration according to claim 19, wherein the matrix forming gelling agent is hydroxypropyl methylcellulose which has a viscosity in the range from 4,000 cps to about 100,000 cps and the concentration of the matrix forming polymer is from about 5% to about 20.0% by weight based on the total weight of the composition.

28. The process of manufacturing the solid pharmaceutical composition for oral administration according to claim 19, wherein the matrix forming gelling agent contains a combination of Methyl Cellulose (Viscosity 3000–5600 cP) and Methyl Cellulose (Viscosity 80000–20000 cP).

29. The process of manufacturing the solid pharmaceutical composition for oral administration according to claim 19, wherein the gas generating component is adapted to generate a gas in contact with gastric fluid, wherein the gelling agent is adapted to form a substantially gas-impermeable gel matrix in the presence of a fluid, and thereby trapping the gas generated effectively causing the device to float in the fluid while the second active agent is released slowly in a controlled manner.

30. The process of manufacturing the solid pharmaceutical composition for oral administration according to claim 19, wherein the floating bilayer system is adapted to be taken into a person's gastric region and upper intestine by being oral administered.

31. The process of manufacturing the solid pharmaceutical composition for oral administration according to claim 19, wherein each layer of the said dosage form additionally comprises an additive selected from the group consisting of magnesium stearate, calcium stearate, zinc stearate, powdered stearic acid, hydrogenated vegetable oils, talc, polyethylene glycol, mineral oil, an FD&C color, modified cellulose, lactose, gelatin, starch paste, acacia, tragacanth, povidone, polyethylene glycol, colloidal silicon dioxide, talc, sodium lauryl sulfate, sodium phosphate, magnesium chloride, magnesium sulfate, magnesium phosphate, microcrystalline cellulose, sodium starch glycolate, lactose, microcrystalline cellulose, sucrose, glucose, mannitol, calcium carbonate, colloidal anhydrous silica, polyethylene glycols, waxes, hydrogenated castor oil, starch, PVP and a combination thereof.

32. The process of manufacturing the solid pharmaceutical composition for oral administration according to claim 19, wherein the active agent in the immediate release layer or the immediate delivery layer and active agent in the controlled release layer or the controlled delivery layer may be same or different and the composition optionally comprises the same active agent in both the layers.

33. The process of manufacturing the solid pharmaceutical composition for oral administration according to claim 19, wherein the total amount of active agent is in the range from about 5% to about 80% of an total active ingredient by weight based on the total weight of the composition.

34. The process of manufacturing the solid pharmaceutical composition for oral administration according to claim 19, wherein the active agent is selected from the group consisting of fluoroquinolone antibiotic ciprofloxacin, ofloxacin, pefloxacin, grepafloxacin, enoxacin, amifloxacin, fleroxacin, temafloxacin, lomefloxacin, norfloxacin, sparfloxacin, levofloxacin, gatifloxacin and moxifloxacin.

35. The process of manufacturing the solid pharmaceutical composition for oral administration according to claim 19, wherein the active agent is ofloxacin.

36. The process of manufacturing the solid pharmaceutical composition for oral administration according to claim 19, wherein the active agent is ciprofloxacin.

37. The process of manufacturing the solid pharmaceutical composition for oral administration according to claim 19, wherein the system may be coated with a polymeric film merely to provide protection from moisture which does not retard the release and said coating polymer is selected from the group consisting of hydroxypropyl methyl cellulose, hydroxypropyl cellulose, polyvinyl pyrrolidone, polyvinyl alcohol or methacrylic acid polymer.

38. The process of manufacturing the solid pharmaceutical composition for oral administration according to claim 19, wherein the polymer for coating is methacrylic acid copolymer and is present in a concentration of from about 1% to about 5.0% by weight based on the total weight of the composition.

39. The composition according to claim 1, wherein the disintegrating agent in the first layer is sodium starch glycolate present in the range of 0.25% to 2.5% by weight based on the total weight of the composition.

40. The process of manufacturing the solid pharmaceutical composition for oral administration according to claim 19, wherein the first layer comprises a disintegrating agent selected from group consisting of starch, sodium starch glycolate, pregelatinished starch, crosslinked polyvinyl pyrrolidone, cross linked carboxy methylcellulose, ion exchange resin, and the sodium starch glycolate is present in an amount ranging from about 0.5 to 2.0% by weight of the total weight of the composition.

* * * * *